(12) United States Patent
Rosenberg et al.

(10) Patent No.: US 9,078,921 B2
(45) Date of Patent: Jul. 14, 2015

(54) PHARMACEUTICALLY ACCEPTABLE SOLUBILIZING COMPOSITION AND PHARMACEUTICAL DOSAGE FORM CONTAINING SAME

(75) Inventors: Jörg Rosenberg, Ellerstadt (DE); Jörg Breitenbach, Mannheim (DE); Kennan Marsh, Lake Forest, IL (US); Bernd Liepold, Heidelberg (DE); Christoph Schmidt, Mannheim (DE); Ute Lander, Dannenfels (DE)

(73) Assignee: Abbvie Deutschland GmbH & Co KG, Wiesbaden (DE)

( * ) Notice: Subject to any disclaimer, the term of this patent is extended or adjusted under 35 U.S.C. 154(b) by 1568 days.

(21) Appl. No.: 12/305,870

(22) PCT Filed: Jul. 17, 2007

(86) PCT No.: PCT/EP2007/057392
§ 371 (c)(1),
(2), (4) Date: Jun. 11, 2010

(87) PCT Pub. No.: WO2008/009689
PCT Pub. Date: Jan. 24, 2008

(65) Prior Publication Data
US 2010/0247635 A1     Sep. 30, 2010

Related U.S. Application Data

(60) Provisional application No. 60/832,074, filed on Jul. 19, 2006.

(30) Foreign Application Priority Data

Jul. 19, 2006 (EP) .................................... 06015076

(51) Int. Cl.
| | | |
|---|---|---|
| *A61P 31/18* | (2006.01) | |
| *A61K 47/34* | (2006.01) | |
| *A61K 9/48* | (2006.01) | |
| *A61K 31/513* | (2006.01) | |
| *A61K 47/22* | (2006.01) | |
| *A61K 9/14* | (2006.01) | |
| *A61K 9/20* | (2006.01) | |
| *A61K 31/427* | (2006.01) | |
| *A61K 47/14* | (2006.01) | |

(52) U.S. Cl.
CPC ................. *A61K 47/22* (2013.01); *A61K 9/145* (2013.01); *A61K 9/146* (2013.01); *A61K 9/2013* (2013.01); *A61K 9/2095* (2013.01); *A61K 31/427* (2013.01); *A61K 31/513* (2013.01); *A61K 47/14* (2013.01); *A61K 9/2027* (2013.01)

(58) Field of Classification Search
CPC .............. A61K 2300/00; A61K 31/47; A61K 31/7072; A61K 31/472; A61K 31/496; A61K 31/506; A61K 31/52; A61K 31/536; A61K 47/12; A61K 47/32; A61K 9/107; A61K 31/39; A61K 31/415; A61K 31/675
See application file for complete search history.

(56) References Cited

U.S. PATENT DOCUMENTS

| | | |
|---|---|---|
| 2004/0013697 A1 | 1/2004 | Berndl et al. |
| 2005/0208082 A1 | 9/2005 | Papas et al. |
| 2005/0236236 A1 | 10/2005 | Farooq et al. |
| 2005/0288326 A1* | 12/2005 | Matsuzaki et al. ............ 514/312 |
| 2006/0264469 A1* | 11/2006 | Breul et al. .................... 514/326 |

FOREIGN PATENT DOCUMENTS

| | | | |
|---|---|---|---|
| FR | 2 861 992 | 5/2005 | |
| WO | WO-97/35587 | 10/1997 | |
| WO | WO-00/57854 | 10/2000 | |
| WO | WO-01/00175 A1 | 1/2001 | |
| WO | WO-01/76561 | 10/2001 | |
| WO | WO-01/91727 A2 | 12/2001 | |
| WO | WO-02/24184 | 3/2002 | |
| WO | WO-2005/039551 | 5/2005 | |
| WO | WO2005/039551 A2 * | 5/2005 | .................... 424/401 |
| WO | WO-2005/041929 | 5/2005 | |
| WO | WO-2005/063209 | 7/2005 | |
| WO | WO2005/063209 A1 * | 7/2005 | .................... 424/401 |
| WO | WO2005063209 A1 * | 7/2005 | .................... 424/401 |
| WO | WO-2006/060817 | 6/2006 | |

OTHER PUBLICATIONS

FR2861992A1, translation abstract and bibliographic data. Published May 13, 2005.*
ISR (PCT/ISA/210) issued in PCT/EP2007/057392, Dec. 27, 2007.
(Continued)

*Primary Examiner* — Audrea Buckley
(74) *Attorney, Agent, or Firm* — Saul Ewing LLP; Peter C. Lauro, Esq.

(57) ABSTRACT

A pharmaceutically acceptable solubilizing composition comprising (i) at least one tocopheryl compound having a polyalkylene glycol moiety and (ii) at least one alkylene glycol fatty acid monoester or mixture of alkylene glycol fatty acid mono- and diester is disclosed. The solubilizing composition is useful in the manufacture of a pharmaceutical dosage form which comprises a melt-processed mixture of at least one active ingredient, at least one pharmaceutically acceptable polymer. The active ingredient(s) may be inhibitors of HIV protease. The solubilizing composition enhances the bioavailability of the active ingredient after oral intake.

20 Claims, No Drawings

(56) References Cited

OTHER PUBLICATIONS

Written Opinion (PCT/ISA/237) issued in PCT/EP2007/057392, Dec. 27, 2007.
Yu L et al: "Vitamin E-TPGS increases absorption flux of an HIV protease inhibitor by enhancing its solubility and permeability" Pharmaceutical Research, New York, NY, US, vol. 16, No. 12, December 1000 (Dec. 1999), pp. 1812-1817, XP002389072, ISSN: 0724-8741, the whole document.
Repka M A et al: "Influence of Vitamin E TPGS on the Properties of Hydrophilic Films Produced by Hot-Melt Extrusion" International Journal of Pharmaceutics, Amsterdam, NL, vol. 202, No. 1/2, Jul. 20, 2000, pp. 63-70, XP001183717, ISSN: 0378-5173.

* cited by examiner

PHARMACEUTICALLY ACCEPTABLE SOLUBILIZING COMPOSITION AND PHARMACEUTICAL DOSAGE FORM CONTAINING SAME

This application is the U.S. national phase, pursuant to 35 U.S.C. §371, of PCT international application Ser. No. PCT/EP2007/057392, filed Jul. 17, 2007, designating the United States and published in English on Jan. 24, 2008 as publication WO 2008/009689 A1, which claims priority to European application Ser. No. 06015076.0, filed Jul. 19, 2006 and U.S. provisional application Ser. No. 60/832,074, filed Jul. 19, 2006. The entire contents of the aforementioned patent applications are incorporated herein by this reference.

The present invention relates to a pharmaceutically acceptable solubilizing composition and pharmaceutical dosage forms containing the same.

A measure of the potential usefulness of an oral dosage form of a pharmaceutical agent is the bioavailability observed after oral administration of the dosage form. Various factors can affect the bioavailability of a drug when administered orally. These factors include aqueous solubility, drug absorption throughout the gastrointestinal tract, dosage strength and first-pass effect. Aqueous solubility is one of the most important of these factors.

For a variety of reasons, such as patient compliance and taste masking, a solid dosage form is usually preferred over a liquid dosage form. In most instances, however, oral solid dosage forms of a drug provide a lower bioavailability than oral solutions of the drug.

There have been attempts to improve the bioavailability provided by solid dosage forms by forming solid solutions of the drug. Solid solutions are preferred physical systems because the components therein readily form liquid solutions when contacted with a liquid medium such as gastric juice. The ease of dissolution may be attributed at least in part to the fact that the energy required for dissolution of the components from a solid solution is less than that required for the dissolution of the components from a crystalline or microcrystalline solid phase. It is, however, important that the drug released from the solid solution remains water-solubilized in the aqueous fluids of the gastrointestinal tract; otherwise, the drug may precipitate in the gastrointestinal tract, resulting in low bioavailability.

WO 01/00175 discloses mechanically stable pharmaceutical dosage forms which are solid solutions of active ingredients in an auxiliary agent matrix. The matrix contains a homopolymer or a copolymer of N-vinyl pyrrolidone and a liquid or semi-solid surfactant.

WO 01/91727 discloses a self-emulsifying active substance formulation comprising at least one active substance and a formulation basis which includes a lipid component, a binder component and optionally additional auxiliary agents.

WO 00/57854 discloses mechanically stable pharmaceutical dosage forms for peroral administration which contain at least one active compound, at least one thermo-plastically mouldable, matrix-forming auxiliary and more than 10 and up to 40% by weight of a surface-active substance that has an HLB of between 2 and 18, is liquid at 20° C., or has a drop point at between 20 and 50° C.

WO 2005/039551 discloses a solid pharmaceutical dosage form providing improved oral bioavailability for inhibitors of HIV protease. The dosage form comprises a solid dispersion of at least one HIV protease inhibitor and at least one pharmaceutically acceptable water-soluble polymer and at least one pharmaceutically acceptable surfactant, said pharmaceutically acceptable water-soluble polymer having a Tg of at least about 50° C. Preferably, the pharmaceutically acceptable surfactant has an HLB value of from about 4 to about 10

US 2005/0208082 discloses a solubilizing composition comprising a mixture of vitamin E TPGS and linoleic acid. The solubilizing composition is used to disperse a lipophile in an aqueous phase. The lipophile may be a therapeutically effective lipophile such as lipophilic vitamins, coenzyme Q10, carotenoids, alpha-lipoic acid, essential fatty acids.

US 2005/0236236 discloses pharmaceutical compositions for administration of hydrophobic drugs, particularly steroids. The pharmaceutical compositions include a hydrophobic drug, a vitamin E substance and a surfactant. The reference claims a synergistic effect between the hydrophobic drug and the vitamin E substance.

There is a continuing need for the development of improved oral solid dosage forms of poorly water-soluble active ingredients that provide suitable oral bioavailability and stability.

The invention provides a pharmaceutically acceptable solubilizing composition comprising (i) at least one tocopheryl compound having a polyalkylene glycol moiety (preferably a polyethylene moiety having a molecular weight in the range of 200 to 6000) and (ii) at least one alkylene glycol fatty acid mono ester or mixture of alkylene glycol fatty acid mono and diester.

In general, the tocopheryl compound corresponds to the formula below

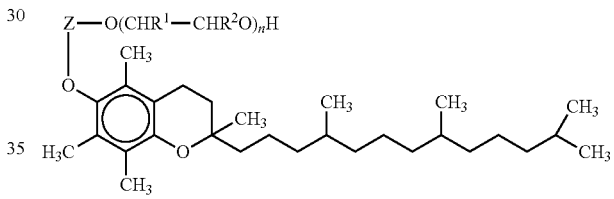

wherein Z is a linking group, $R^1$ and $R^2$ are, independently of one another, hydrogen or $C_1$-$C_4$ alkyl and n is an integer from 5 to 100, preferably 10 to 50. Typically, Z is the residue of an aliphatic dibasic acid such as glutaric, succinic, or adipic acid. Preferably, both $R^1$ and $R^2$ are hydrogen.

The preferred tocopheryl compound is alpha tocopheryl polyethylene glycol succinate, which is commonly abbreviated as vitamin E TPGS. Vitamin E TPGS is a water-soluble form of natural-source vitamin E prepared by esterifying d-alpha-tocopheryl acid succinate with polyethylene glycol 1000. Vitamin E TPGS is available from Eastman Chemical Company, Kingsport, Tenn., USA and is listed in the US pharmacopoeia (NF).

The preferred alkylene glycol fatty acid mono ester is a propylene glycol fatty acid mono ester, such as propylene glycol monolaurate (available under the trade name LAUROGLYCOL® from Gattefossé, France). Commercially available propylene glycol lauric acid mono ester products consist of a mixture of mono- and dilaurate. Two propylene glycol monolaurate products are specified in the European Pharmacopoea (referenced "type I" and "type II" respectively). Both types are suitable for carrying out the present invention, with propylene glycol monolaurate "type I" being the most preferred. This "type I" product having a HLB value of about 4 consists of a mixture having between 45 and up to 70% mono-laurate and between 30 and up to 55% of di-laurate. The "type II" product is specified according to Pharm. Eur. as having a minimum of 90% mono-laurate and a maximum of 10% of di-laurate.

Where a mixture of alkylene glycol fatty acid mono and diester is employed, this preferably contains at least 40% by weight of the mono ester, especially 45 to 95% by weight, relative to the weight of the ester mixture.

Preferably, the weight ratio of tocopheryl compound and alkylene glycol fatty acid mono ester (or mixture of alkylene glycol fatty acid mono and diester) is in the range of from 9:1 to 1:9, in particular from 5:1 to 1:5.

In a second aspect, the invention provides a pharmaceutical dosage form which comprises a melt-processed mixture of at least one active ingredient, at least one pharmaceutically acceptable polymer and a solubilizing composition, the solubilizing composition comprising (i) at least one tocopheryl compound having a polyalkylene glycol moiety and (ii) at least one alkylene glycol fatty acid mono ester mixture of alkylene glycol fatty acid mono- and diester.

In general, dosage forms of the invention comprise, relative to the weight of the melt-processed mixture, from about 0.5 to 40% by weight of an active ingredient or a combination of active ingredient(s), 40 to 99% by weight of the pharmaceutically acceptable polymer (or any combination of such polymers), 0.5 to 20% by weight of the solubilizing composition, and 0 to 15% by weight of additives.

Preferred dosage forms of the invention comprise, relative to the weight of the melt-processed mixture, from about 15 to 40% by weight (preferably 25 to 36% by weight, most preferably 28 to 35% by weight) of an active ingredient or a combination of active ingredient(s), 40 to 70% by weight (preferably 50 to 60% by weight) of the pharmaceutically acceptable polymer (or any combination of such polymers), 4 to 20% by weight (preferably 5 to 10% by weight) of the solubilizing composition, and 0 to 15% by weight of additives.

Especially where highly efficient active ingredients are concerned, dosage forms of the invention may comprise, relative to the weight of the melt-processed mixture, from about 0.5 to 15% by weight (preferably 2 to 10% by weight) of an active ingredient or a combination of active ingredient(s), 60 to 99% by weight (preferably 70 to 95% by weight) of the pharmaceutically acceptable polymer (or any combination of such polymers), 0.5 to 15% by weight (preferably 3 to 10% by weight) of the solubilizing composition, and 0 to 15% by weight of additives.

In the dosage forms of the invention, the active ingredient is present as a solid dispersion or, preferably, as a solid solution. The term "solid dispersion" defines a system in a solid state (as opposed to a liquid or gaseous state) comprising at least two components, wherein one component is dispersed evenly throughout the other component or components. For example, the active ingredient or combination of active ingredients is dispersed in a matrix comprised of the pharmaceutically acceptable polymer(s) and pharmaceutically acceptable solubilizers. The term "solid dispersion" encompasses systems having small particles, typically of less than 1 μm in diameter, of one phase dispersed in another phase. When said dispersion of the components is such that the system is chemically and physically uniform or homogenous throughout or consists of one phase (as defined in thermodynamics), such a solid dispersion will be called a "solid solution" or a "glassy solution". A glassy solution is a homogeneous, glassy system in which a solute is dissolved in a glassy solvent. Glassy solutions and solid solutions are preferred physical systems. These systems do not contain any significant amounts of active ingredients in their crystalline or microcrystalline state, as evidenced by thermal analysis (DSC) or X-ray diffraction analysis (WAXS).

Active ingredients used in the process according to the present invention are biologically active agents and include those which exert a local physiological effect, as well as those which exert a systemic effect, after oral administration. The invention is particularly useful for water-insoluble or poorly water-soluble (or "hydrophobic" or "lipophilic") compounds. Compounds are considered water-insoluble or poorly water-soluble when their solubility in water at 25° C. is less than 1 g/100 ml, especially less than 0.1 g/100 ml.

Examples of suitable active substances include, but are not limited to:

analgesic and anti-inflammatory drugs such as fentanyl, indomethacin, ibuprofen, naproxene, diclofenac, diclofenac sodium, fenoprofen, acetylsalicylic acid, ketoprofen, nabumetone, paracetamol, piroxicam, meloxicam, tramadol, and COX-2 inhibitors such as celecoxib and rofecoxib;

anti-arrhythmic drugs such as procainamide, quinidine and verapamil;

antibacterial and antiprotozoal agents such as amoxicillin, ampicillin, benzathine penicillin, benzylpenicillin, cefaclor, cefadroxil, cefprozil, cefuroxime axetil, cephalexin, chloramphenicol, chloroquine, ciprofloxacin, clarithromycin, clavulanic acid, clindamycin, doxyxycline, erythromycin, flucloxacillin sodium, halofantrine, isoniazid, kanamycin sulphate, lincomycin, mefloquine, minocycline, nafcillin sodium, nalidixic acid, neomycin, nortloxacin, ofloxacin, oxacillin, phenoxymethyl-penicillin potassium, pyrimethamine-sulfadoxime and streptomycin;

anti-coagulants such as warfarin;

antidepressants such as amitriptyline, amoxapine, butriptyline, clomipramine, desipramine, dothiepin, doxepin, fluoxetine, reboxetine, aminoptine, selegiline, gepirone, imipramine, lithium carbonate, mianserin, milnacipran, nortriptyline, paroxetine, sertraline and 3-[2-[3,4-dihydrobenzofuro[3,2-c]pyridin-2(1H)-yl]ethyl]-2-methyl-4H-pyrido[1,2-a]pyrimidin-4-one;

anti-diabetic drugs such as glibenclamide and metformin;

anti-epileptic drugs such as carbamazepine, clonazepam, ethosuximide, gabapentin, lamotrigine, levetiracetam, phenobarbitone, phenyloin, primidone, tiagabine, topiramate, valpromide and vigabatrin;

antifungal agents such as amphotericin, clotrimazole, econazole, fluconazole, flucytosine, griseofulvin, itraconazole, ketoconazole, miconazole nitrate, nystatin, terbinafine and voriconazole;

antihistamines such as astemizole, cinnarizine, cyproheptadine, decarboethoxyloratadine, fexofenadine, flunarizine, levocabastine, loratadine, norastemizole, oxatomide, promethazine and terfenadine;

anti-hypertensive drugs such as captopril, enalapril, ketanserin, lisinopril, minoxidil, prazosin, ramipril, reserpine, terazosin and telmisartan;

anti-muscarinic agents such as atropine sulphate and hyoscine;

antineoplastic agents and antimetabolites such as platinum compounds, such as cisplatin and carboplatin; taxanes such as paclitaxel and docetaxel; tecans such as camptothecin, irinotecan and topotecan; vinca alkaloids such as vinblastine, vindecine, vincristine and vinorelbine; nucleoside derivatives and folic acid antagonists such as 5-fluorouracil, capecitabine, gemcitabine, mercaptopurine, thioguanine, cladribine and methotrexate; alkylating agents such as the nitrogen mustards, e.g. cyclophosphamide, chlorambucil, chiormethine, iphosphamide, melphalan, or the nitrosoureas, e.g. carmustine, lomustine, or other alkylating agents, e.g. busulphan, dacarbazine, procarbazine, thiotepa; antibiotics such as daunorubicin, doxorubicin, idarubicin, epirubicin, bleomycin, dactinomycin and mitomycin; HER 2 antibodies such as trastuzumab; podophyllotoxin derivatives such as etoposide and teniposide; farnesyl transferase inhibitors; anthrachinon derivatives such as mitoxantron;

anti-migraine drugs such as alniditan, naratriptan and sumatriptan;

anti-Parkinsonian drugs such as bromocryptine mesylate, levodopa and selegiline;

antipsychotic, hypnotic and sedating agents such as alprazolam, buspirone, chlordiazepoxide, chlorpromazine, clozapine, diazepam, flupenthixol, fluphenazine, flurazepam, 9-hydroxyrisperidone, lorazepam, mazapertine, olanzapine, oxazepam, pimozide, pipamperone, piracetam, promazine, risperidone, selfotel, seroquel, sertindole, sulpiride, temazepam, thiothixene, triazolam, trifluperidol, ziprasidone and zolpidem;

anti-stroke agents such as lubeluzole, lubeluzole oxide, rilutozole, aptiganel, eliprodil and remacemide;

antitussives such as dextromethorphan and laevodropropizine;

antivirals such as acyclovir, ganciclovir, loviride, tivirapine, zidovudine, lamivudine, zidovudine/lamivudine, didanosine, zalcitabine, stavudine, abacavir, lopinavir, amprenavir, nevirapine, efavirenz, delavirdine, indinavir, nelfinavir, ritonavir, saquinavir, adefovir and hydroxyurea;

beta-adrenoceptor blocking agents such as atenolol, carvedilol, metoprolol, nebivolol and propanolol;

cardiac inotropic agents such as aminone, digitoxin, digoxin and milrinone;

corticosteroids such as beclomethasone dipropionate, betamethasone, budesonide, dexamethasone, hydrocortisone, methylprednisolone, prednisolone, prednisone and triamcinolone;

disinfectants such as chlorhexidine;

diuretics such as acetazolamide, furosemide, hydrochlorothiazide and isosorbide;

enzymes;

essential oils such as anethole, anise oil, caraway, cardamom, cassia oil, cineole, cinnamon oil, clove oil, coriander oil, dementholised mint oil, dill oil, eucalyptus oil, eugenol, ginger, lemon oil, mustard oil, neroli oil, nutmeg oil, orange oil, peppermint, sage, spearmint, terpineol and thyme;

gastro-intestinal agents such as cimetidine, cisapride, clebopride, diphenoxylate, domperidone, famotidine, lansoprazole, loperamide, loperamide oxide, mesalazine, metoclopramide, mosapride, nizatidine, norcisapride, olsalazine, omeprazole, pantoprazole, perprazole, prucalopride, rabeprazole, ranitidine, ridogrel and sulphasalazine;

haemostatics such as aminocaproic acid;

lipid regulating agents such as atorvastatin, fenofibrate, fenofibric acid, lovastatin, pravastatin, probucol and simvastatin;

local anaesthetics such as benzocaine and lignocaine;

opioid analgesics such as buprenorphine, codeine, dextromoramide, dihydrocodeine, hydrocodone, oxycodone and morphine;

parasympathomimetics and anti-dementia drugs such as AIT-082, eptastigmine, galanthamine, metrifonate, milameline, neostigmine, physostigmine, tacrine, donepezil, rivastigmine, sabcomeline, talsaclidine, xanomeline, memantine and lazabemide;

peptides and proteins such as antibodies, becaplermin, cyclosporine, tacrolimus, erythropoietin, immunoglobulins and insuline;

sex hormones such as oestrogens: conjugated oestrogens, ethinyloestradiol, mestranol, oestradiol, oestriol, oestrone; progestogens; chlormadinone acetate, cyproterone acetate, 17-deacetyl norgestimate, desogestrel, dienogest, dydrogesterone, ethynodiol diacetate, gestodene, 3-keto desogestrel, levonorgestrel, lynestrenol, medroxy-progesterone acetate, megestrol, norethindrone, norethindrone acetate, norethisterone, norethisterone acetate, norethynodrel, norgestimate, norgestrel, norgestrienone, progesterone and quingestanol acetate;

stimulating agents such as sildenafil, vardenafil;

vasodilators such as amlodipine, buflomedil, amyl nitrite, diltiazem, dipyridamole, glyceryl trinitrate, isosorbide dinitrate, lidoflazine, molsidomine, nicardipine, nifedipine, oxpentifylline and pentaerythritol tetranitrate;

their N-oxides, their pharmaceutically acceptable acid or base addition salts and their stereochemically isomeric forms.

Pharmaceutically acceptable acid addition salts comprise the acid addition salt forms which can be obtained conveniently by treating the base form of the active ingredient with appropriate organic and inorganic acids.

Active ingredients containing an acidic proton may be converted into their non-toxic metal or amine addition salt forms by treatment with appropriate organic and inorganic bases.

The term addition salt also comprises the hydrates and solvent addition forms which the active ingredients are able to form. Examples of such forms are hydrates, alcoholates and the like.

The N-oxide forms of the active ingredients comprise those active ingredients in which one or several nitrogen atoms are oxidized to the so-called N-oxide.

The term "stereochemically isomeric forms" defines all possible stereoisomeric forms which the active ingredients may possess. In particular, stereogenic centers may have the R- or S-configuration and active ingredients containing one or more double bonds may have the E- or Z-configuration.

In an embodiment of the invention, the active ingredient is an HIV protease inhibitor or a combination of HIV protease inhibitors.

Examples of HIV protease inhibiting compounds include:

2S,3S,5S)-5-(N-(N-((N-methyl-N-((2-isopropyl-4-thiazolyl)methyl)amino)carbonyl)-L-valinyl)amino-2-(N-((5-thiazolyl)methoxy-carbonyl)-amino)-amino-1,6-diphenyl-3-hydroxyhexane (ritonavir);

(2S,3S,5S)-2-(2,6-Dimethylphenoxyacetyl)amino-3-hydroxy-5-[2S-(1-tetrahydro-pyrimid-2-onyl)-3-methylbutanoyl]amino-1,6-diphenylhexane (lopinavir);

N-(2(R)-hydroxy-1(S)-indanyl)-2(R)-phenylmethyl-4(S)-hydroxy-5-(I-(4-(3-pyridylmethyl)-2(S)-N'-(t-butylcarboxamido)-piperazinyl))-pentaneamide (indinavir);

N-tert-butyl-decahydro-2-[2(R)-hydroxy-4-phenyl-3(S)-[[N-(2-quinolylcarbonyl)-L-asparaginyl]amino]butyl]-(4aS,8aS)-isoquinoline-3(S)-carboxamide (saquinavir);

5(S)-Boc-amino-4(S)-hydroxy-6-phenyl-2(R)phenylmethylhexanoyl-(L)-Val-(L)-Phe-morpholin-4-ylamide;

1-Naphthoxyacetyl-beta-methylthio-Ala-(2S,3S)-3-amino-2-hydroxy-4-butanoyl 1,3-thiazolidine-4t-butylamide;

5-isoquinolinoxyacetyl-beta-methylthio-Ala-(2S,3S)-3-amino-2-hydroxy-4-butanoyl-1,3-thiazolidine-4-t-butylamide;

[1S-[1R-(R-),2S*])-N'-[3-[[[(1,1-dimethylethyl)amino]carbonyl](2-methylpropyl)amino]-2hydroxy-1-(phenylmethyl)propyl]-2-[(2-quinolinylcarbonyl)amino]-butanediamide;

amprenavir (VX-478); DMP-323; DMP-450; AG1343 (nelfinavir);
atazanavir (BMS 232,632);
tipranavir;
palinavir;
darunavir (TMC-114);
RO033-4649;
fosamprenavir (GW433908);
P-1946;
tert-butyl [3-hydroxy-4-[2-hydroxy-4-[4-(morpholin-4-yl-carbonylmethoxy)phenyl]-3-tert-butoxycarbonylamino-butyl]amino-1-phenyl-butan-2-yl]aminoformate (BMS 186,318);
SC-55389a; BILA 1906 BS;
N-[3-[1-(2-hydroxy-4-oxo-6-phenethyl-6-propyl-5H-pyran-3-yl)propyl]phenyl]-5-(trifluoromethyl)pyridine-2-sulfonamide (tipranavir, U-140690);
or combinations thereof.

A preferred compound is an HIV protease inhibitor marketed by Abbott Laboratories under the tradename Norvir, with the common name ritonavir [(2S,3S,5S)-5-(N-(N-((N-methyl-N-((2-isopropyl-4-thiazolyl)-methyl)amino) carbonyl)L-valinyl)amino-2-(N-((5-thiazolyl)methoxy-carbonyl)-amino)-1,6-diphenyl-3-hydroxyhexane]. This and other compounds as well as methods for preparing same are disclosed in U.S. Pat. Nos. 5,648,497 and 5,541,206, the disclosures of which are incorporated herein by reference.

Additional HIV protease inhibitors which may be formulated into the dosage form of the invention include a compound known as lopinavir ((2S,3S,5S)-2-(2,6-dimethyl-phenoxyacetyl)-amino-3-hydroxy-5-(2S-(1-tetrahydropyrimid-2-onyl)-3-methylbutanoyl)-amino-1,6-diphenylhexane).
This and other compounds, as well as methods for preparing same, are identified in U.S. Pat. No. 5,914,332, the disclosure of which is incorporated herein by reference.

A compound known as nelfinavir mesylate (marketed under the tradename Viracept by Agouron Pharmaceuticals, Inc. in La Jolla, Calif.) is another HIV protease inhibitor which may be formulated into the dosage form of the invention.

The dosage forms of the present invention exhibit a release and absorption behaviour that is characterized by high attainable AUC, high attainable $C_{max}$ (maximum plasma concentration), and low $T_{max}$ (time to reach maximum plasma concentration).

The term "AUC" means "Area Under the Curve" and is used in its normal meaning, i.e. as the area under the plasma concentration-time curve from 0 to 24 hours, where the dosage form has been administered orally to dogs (beagle) under non-fasting conditions. "Non-fasting condition" means that the dogs receive a nutritionally balanced daily ration during the pre-test period and the whole test period. The AUC has units of concentration times time. Once the experimental concentration-time points have been determined, the AUC may conveniently be calculated, e.g. by a computer program or by the trapezoidal method.

The dosage forms according to the invention are characterized by an excellent stability and, in particular, exhibit high resistance against recrystallization or decomposition of the active ingredient(s).

The pharmaceutically acceptable polymer may be selected from water-soluble polymers, water-dispersible polymers or water-swellable polymers or any mixture thereof. Polymers are considered water-soluble if they form a clear homogeneous solution in water. When dissolved at 20° C. in an aqueous solution at 2% (w/v), the water-soluble polymer preferably has an apparent viscosity of 1 to 5000 mPa·s, more preferably of 1 to 700 mPa·s, and most preferably of 5 to 100 mPa·s. Water-dispersible polymers are those that, when contacted with water, form colloidal dispersions rather than a clear solution. Upon contact with water or aqueous solutions, water-swellable polymers typically form a rubbery gel.

Preferably, the pharmaceutically acceptable polymer employed in the invention has a Tg of at least 40° C., preferably at least +50° C., most preferably from 80° to 180. ° C.

"Tg" means glass transition temperature. Methods for determining Tg values of the organic polymers are described in "Introduction to Physical Polymer Science", 2nd Edition by L. H. Sperling, published by John Wiley & Sons, Inc., 1992. The Tg value can be calculated as the weighted sum of the Tg values for homopolymers derived from each of the individual monomers, i, that make up the polymer: Tg=$\Sigma W_i X_i$ where W is the weight percent of monomer i in the organic polymer, and X is the Tg value for the homopolymer derived from monomer i. Tg values for the homopolymers may be taken from "Polymer Handbook", 2nd Edition by J. Brandrup and E. H. Immergut, Editors, published by John Wiley & Sons, Inc., 1975.

Various additives contained in the melt-processed mixture or even the active ingredient(s) itself may exert a plasticizing effect on the polymer and thus depress the Tg of the polymer such that the final melt-processed mixture has a somewhat lower Tg than the starting polymer used for its preparation. In general, the final melt-extruded mixture has a Tg of 10° C. or higher, preferably 15° C. or higher, more preferably 20° C. or higher and most preferred 30° C. or higher.

A melt-processed mixture having a Tg as defined above is mechanically stable and, within ordinary temperature ranges, sufficiently temperature stable so that the melt-processed mixture may be used as dosage forms without further processing or be compacted to tablets with only a small amount of tabletting aids.

For example, preferred pharmaceutically acceptable polymers can be selected from the group comprising
homopolymers and copolymers of N-vinyl lactams, especially homopolymers and copolymers of N-vinyl pyrrolidone, e.g. polyvinylpyrrolidone (PVP), copolymers of N-vinyl pyrrolidone and vinyl acetate or vinyl propionate,
cellulose esters and cellulose ethers, in particular methylcellulose and ethylcellulose, hydroxyalkylcelluloses, in particular hydroxypropylcellulose, hydroxyalkylalkylcelluloses, in particular hydroxypropylmethylcellulose, cellulose phthalates or succinates, in particular cellulose acetate phthalate and hydroxypropylmethylcellulose phthalate, hydroxypropylmethylcellulose succinate or hydroxypropylmethylcellulose acetate succinate;
high molecular polyalkylene oxides such as polyethylene oxide and polypropylene oxide and copolymers of ethylene oxide and propylene oxide,
polyvinyl alcohol-polyethylene glycol-graft copolymers (available as Kollicoat® IR from BASF AG, Ludwigshafen, Germany);
polyacrylates and polymethacrylates such as methacrylic acid/ethyl acrylate copolymers, methacrylic acid/methyl methacrylate copolymers, butyl methacrylate/2-dimethylaminoethyl methacrylate copolymers, poly(hydroxyalkyl acrylates), poly(hydroxyalkyl methacrylates),
polyacrylamides,
vinyl acetate polymers such as copolymers of vinyl acetate and crotonic acid, partially hydrolyzed polyvinyl acetate (also referred to as partially saponified "polyvinyl alcohol"),
polyvinyl alcohol,
oligo- and polysaccharides such as carrageenans, galactomannans and xanthan gum, or mixtures of one or more thereof.

Among these, homopolymers or copolymers of N-vinyl pyrrolidone, in particular a copolymer of N-vinyl pyrrolidone and vinyl acetate, are preferred. A particularly preferred polymer is a copolymer of 60% by weight of the copolymer, N-vinyl pyrrolidone and 40% by weight of the copolymer, vinyl acetate.

The dosage forms of the invention are preferably prepared by melt-extrusion. The melt-extrusion process comprises the steps of preparing a homogeneous melt of the active ingredient or the combination of active ingredients, the pharmaceutically acceptable polymer and the solubilizers, and cooling the melt until it solidifies. "Melting" means a transition into a liquid or rubbery state in which it is possible for one component to become homogeneously embedded in the other. Typically, one component will melt and the other components will dissolve in the melt, thus forming a solution. Melting usually involves heating above the softening point of the pharmaceutically acceptable polymer. The preparation of the melt can take place in a variety of ways. The mixing of the components can take place before, during or after the formation of the melt. For example, the components can be mixed first and then melted or simultaneously mixed and melted. Usually, the melt is homogenized in order to disperse the active ingredients efficiently. Also, it may be convenient first to melt the pharmaceutically acceptable polymer and then to admix and homogenize the active ingredients.

Usually, the melt temperature is in the range of 70 to 250° C., preferably 80 to 180° C., most preferably 100 to 140° C.

The active ingredients can be employed as such or as a solution or dispersion in a suitable solvent such as alcohols, aliphatic hydrocarbons or esters. Another solvent which can be used is liquid carbon dioxide. The solvent is removed, e.g. evaporated, upon preparation of the melt.

Various additives may be included in the melt, for example flow regulators such as colloidal silica; lubricants, bulking agents (fillers), disintegrants, plasticizers, stabilizers such as antioxidants, light stabilizers, radical scavengers, or stabilizers against microbial attack.

The melting and/or mixing takes place in an apparatus customary for this purpose. Particularly suitable are extruders or kneaders. Suitable extruders include single screw extruders, intermeshing screw extruders or else multiscrew extruders, preferably twin screw extruders, which can be corotating or counterrotating and, optionally, equipped with kneading disks or other screw elements for mixing or dispersing the melt. It will be appreciated that the working temperatures will also be determined by the kind of extruder or the kind of configuration within the extruder used. Part of the energy needed to melt, mix and dissolve the components in the extruder can be provided by heating elements. However, the friction and shearing of the material in the extruder may also provide a substantial amount of energy to the mixture and aid in the formation of a homogeneous melt of the components.

The extrudate exiting from the extruder ranges from pasty to viscous. Before allowing the extrudate to solidify, the extrudate may be directly shaped into virtually any desired shape. Shaping of the extrudate may be conveniently carried out by a calender with two counter-rotating rollers with mutually matching depressions on their surface. A broad range of tablet forms can be attained by using rollers with different forms of depressions. If the rollers do not have depressions on their surface, films can be obtained. Alternatively, the extrudate is moulded into the desired shape by injection-moulding. Alternatively, the extrudate is subjected to profile extrusion and cut into pieces, either before (hot-cut) or after solidification (cold-cut).

Additionally, foams can be formed if the extrudate contains a propellant such as a gas, e.g. carbon dioxide, or a volatile compound, e.g. a low molecular-weight hydrocarbon, or a compound that is thermally decomposable to a gas. The propellant is dissolved in the extrudate under the relatively high pressure conditions within the extruder and, when the extrudate emerges from the extruder die, the pressure is suddenly released. Thus the solvability of the propellant is decreased and/or the propellant vaporises so that a foam is formed.

Optionally, the resulting solid solution product is milled or ground to granules. The granules may then be filled into capsules or may be compacted. Compacting means a process whereby a powder mass comprising the granules is densified under high pressure in order to obtain a compact with low porosity, e.g. a tablet. Compression of the powder mass is usually done in a tablet press, more specifically in a steel die between two moving punches.

At least one additive selected from flow regulators, disintegrants, bulking agents (fillers) and lubricants is preferably used in compacting the granules. Disintegrants promote a rapid disintegration of the compact in the stomach and keep the liberated granules separate from one another. Suitable disintegrants are crosslinked polymers such as crosslinked polyvinyl pyrrolidone and crosslinked sodium carboxymethyl cellulose. Suitable bulking agents (also referred to as "fillers") are selected from lactose, calcium hydrogenphosphate, microcrystalline cellulose (Avicel®), magnesium oxide, potato or corn starch, isomalt, polyvinyl alcohol.

Suitable flow regulators are selected from highly dispersed silica (Aerosil®), and animal or vegetable fats or waxes.

A lubricant is preferably used in compacting the granules. Suitable lubricants are selected from polyethylene glycol (e.g., having a Mw of from 1000 to 6000), magnesium and calcium stearates, sodium stearyl fumarate, talc, and the like.

Various other additives may be used, for example dyes such as azo dyes, organic or inorganic pigments such as aluminium oxide or titanium dioxide, or dyes of natural origin; stabilizers such as antioxidants, light stabilizers, radical scavengers, or stabilizers against microbial attack.

Dosage forms according to the invention may be provided as dosage forms consisting of several layers, for example laminated or multilayer tablets. They can be in open or closed form. "Closed dosage forms" are those in which one layer is completely surrounded by at least one other layer. Multilayer forms have the advantage that two active ingredients which are incompatible with one another can be processed, or that the release characteristics of the active ingredient(s) can be controlled. For example, it is possible to provide an initial dose by including an active ingredient in one of the outer layers, and a maintenance dose by including the active ingredient in the inner layer(s). Multilayer tablets types may be produced by compressing two or more layers of granules. Alternatively, multilayer dosage forms may be produced by a process known as "coextrusion". In essence, the process comprises the preparation of at least two different melt compositions as explained above, and passing these molten compositions into a joint coextrusion die. The shape of the coextrusion die depends on the required drug form. For example, dies with a plain die gap, called slot dies, and dies with an annular slit are suitable.

In order to faciliate the intake of such a dosage form by a mammal, it is advantageous to give the dosage form an appropriate shape. Large tablets that can be swallowed comfortably are therefore preferably elongated rather than round in shape.

A film coat on the tablet further contributes to the ease with which it can be swallowed. A film coat also improves taste and provides an elegant appearance. If desired, the film coat may be an enteric coat. The film coat usually includes a polymeric film-forming material such as hydroxypropyl methylcellulose, hydroxypropyl cellulose, and acrylate or methacrylate copolymers. Besides a film-forming polymer, the film coat may further comprise a plasticizer, e.g. polyethylene glycol, a surfactant, e.g. a Tween® type, and optionally a pigment, e.g. titanium dioxide or iron oxides. The film-coating may also comprise talc as anti-adhesive. The film coat usually accounts for less than about 5% by weight of the dosage form.

The exact dose and frequency of administration depends on the particular condition being treated, the age, weight and general physical condition of the particular patient as well as other medication the individual may be taking, as is well known to those skilled in the art.

The following examples will serve to further illustrate the invention without limiting it.

EXAMPLES 1 TO 10

A powdery mixture of copovidone (N-vinyl pyrrolidone/ vinyl acetate copolymer 60:40; 61% by weight), ritonavir (6% by weight), lopinavir (24% by weight) and colloidal silica (1% by weight) was fed into a co-rotating twin-screw extruder (Leistritz Micro 18) together with 8% by weight of a solubilizing agent or a combination of solubilizing agents as reported in table 1 below. The mixture was extruded at a rate of 1 to 2 kg/h and a melt temperature of 120° C. The extrudate was shaped into tablets by calendering between two counter-rotating rollers having depressions on their surface.

Protocol for Drug Dissolution Studies

Drug dissolution studies were conducted according to USP paddle dissolution apparatus #2 at a paddle speed of 75 rpm with 0.06 M POE lauryl ether.

Protocol for the Oral Bioavailability Studies

Dogs (beagle dogs, mixed sexes, weighing approximately 10 kg) received a balanced diet with 27% fat and were permitted water ad libitum. Each dog received a 100 μg/kg subcutaneous dose of histamine approximately 30 minutes prior to dosing. A single dose corresponding to 200 mg lopinavir and 50 mg ritonavir, respectively, was administered to each dog. The dose was followed by approximately 10 milliliters of water. Blood samples were obtained from each animal prior to dosing and 0.25, 0.5, 1.0, 1.5, 2, 3, 4, 6, 8, 10, 12 and 24 hours after drug administration. The plasma was separated from the red cells by centrifugation and frozen (−30° C.) until analysis. Concentrations of HIV protease inhibitors were determined by reverse phase HPLC with low wavelength UV detection following liquid-liquid extraction of the plasma samples. The area under the curve (AUC) was calculated by the trapezoidal method over the time course of the study. Each dosage form was evaluated in a group containing 10-12 dogs; the values reported are averages for each group of dogs. The values are reported as relative bioavailability, compared to the bioavailability of a commercially available lopinavir/ritonavir dosage form (containing lopinavir/ritonavir (20.83% by weight), Span 20 (7% by weight) and copovidone).

The results of the drug dissolution and oral bioavailability studies are reported in table 1 below. No evidence of a crystalline drug in the dosage form could be detected. The glass transition temperature Tg of the extrudate of example 4 was found to be about 50° C.

It is evident that the use of a single solubilizer does not provide adequate bioavailability. Addition of a second solubilizer to lauroglycol greatly improves the attainable bioavailability. The combination of lauroglycol and TPGS yields the highest bioavailability.

TABLE 1

| | Example | | | | | | | | | |
|---|---|---|---|---|---|---|---|---|---|---|
| | 1 | 2 | 3 | 4 | 5 | 6 | 7 | 8 | 9 | 10 |
| | Solubilizing agent(s) | | | | | | | | | |
| | 5% Span 20 3% TPGS* | 5% Span 20 3% Tween 20 | 5% Lauroglycol 3% Tween 20 | 5% Lauroglycol 3% TPGS* | 3% Lauroglycol 5% TPGS* | 5% Lauroglycol 3% Lecithin | 5% Lauroglycol 3% Cremophor | 8% Span 20 | 8% TPGS | 8% Lauroglycol |
| Dissolution | | | | | | | | | | |
| 15 min | 20 | 27 | 36 | 15 | 11 | 25 | 11 | 22 | 2 | 25 |
| 30 min | 49 | 57 | 67 | 32 | 26 | 52 | 25 | 50 | 9 | 48 |
| 60 min | 87 | 93 | 94 | 57 | 53 | 86 | 51 | 86 | 35 | 77 |
| 90 min | 94 | 98 | 97 | 74 | 73 | 96 | 71 | 93 | 62 | 90 |
| 120 min | 96 | 98 | 97 | 86 | 86 | 97 | 84 | 94 | 80 | 94 |
| 150 min | 96 | 99 | 97 | 91 | 93 | 97 | 92 | 94 | 90 | 96 |
| AUC | | | | | | | | | | |
| Lopinavir | 0.36 | 0.11 | 0.73 | 2.29 | 2.1 | 1.38 | 1.60 | 0.61 | 0.005 | 0.80 |
| Ritonavir | 0.28 | 0.06 | 0.58 | 4.81 | 4.6 | 2.04 | 2.94 | 0.40 | 0.005 | 0.82 |

*tocopheryl polyethylene glycol 1000 succinate

We claim:

1. A pharmaceutical dosage form which comprises a melt-processed mixture of at least one active ingredient that is present as a solid dispersion, at least one pharmaceutically acceptable homopolymer or copolymer of N-vinylpyrrolidone and a solubilizing composition, the solubilizing composition comprising (i) at least one tocopheryi compound having a polyalkylene glycol moiety and (ii) at least one alkylene glycol fatty acid monoester or mixture of alkylene glycol fatty acid mono- and diester,
wherein said dosage form comprises, relative o the weight of the melt-processed mixture, from about 0.5 to 40% by weight of said active ingredient, 40 to 99% by weight of said pharmaceutically acceptable homopolymer or copolymer of N-vinylpyrrolidone, 0.5 to 20% by weight of said solubilizing composition, and 0 to 15% by weight of additives.

2. The dosage form of claim 1, wherein the tocopheryl omcompound is alpha tocopheryl polyethylene glycol succinate.

3. The dosage form of claim 1, wherein the alkalkylene glycol fatty acid monoester is propylene glycol monolaurate.

4. The dosage form of claim 1, wherein the weight ratio of tocopheryl compound and alkylene glycol fatty acid ester is in the range of from 9:1 to 1:9.

5. The dosage form of claim 1 which comprises, relative to the weight of the melt-processed mixture, from about 15 to 40% by weight of said active ingredient, 40 to 70% by weight of said pharmaceutically acceptable homopolymer or copolymer of N-vinylpyrrolidone, 4 to 20% by weight of said solubilizing composition, and 0 to 15% by weight of the additives.

6. The dosage form of claim 1 which comprises, relative to the weight of the melt-processed mixture, from about 0.5 to 15% by weight of said active ingredient, 60 to 99% by weight of said pharmaceutically acceptable homopolymer or copolymer of N-vinylpyrrolidone, 0.5 to 15% by weight of said solubilizing composition, and 0 to 15% by weight of the additives.

7. The dosage form of claim 1, wherein the active ingredient is an HIV protease inhibitor or a combination of HIV protease inhibitors.

8. The dosage form of claim 7, wherein said HIV protease inhibitor is selected from the group consisting of:
  (2S,3S,5S)-5-(N—(N—((N-methyl-N-((2-isopropyl-4-thiazolyl)methy)amino)carbonyl)-L-valinyl)amino-2-(N-((5-thiazolyl)methoxy-carbonyl)-amino)-amino-1,6-diphenyl-3-hydroxyhexane (ritonavir);
  (2S,3S,5S)-2-(2,6-dimethyl-phenoxyacetyl)-amino-3-hydroxy-5-[2S-(l1-tetrahydro-pyrimid-2-onyl)-3-methylbutanoyl]amino-1,6-diphenylhexane (lopinavir);
  N-(2(R)-hydroxy-1(S)-indanyl)-2(R)-phenylmethyl-4(S) hydroxy-5-(l1-(4-(3-pyridylmethyl)-2(S)-N'-(t-butyloarboxamido)-piperazinyl))-penteneamide (indinavir);
  N-tert-butyl-decahydro-2[2(R)-hydroxy-4-phenyl-3(S)-[[N-(2-quinolylcarbonyl)-L-asparaginyi]-amino]butyl]-(4aS,8aS)-isoquinoline-3(S)-carboxamide (saquinavir);
  5(S)-Boc-amino-4(S)hydroxy-6-phenyl-2(R)-phenylmethyl-hexanoyl(L)-Val-(L)-Phe-morpholin-4-ylamide;
  1-Naphthoxyacetyl-beta-methylthio-Ala-(2S,3S)-3-amino-2-hydroxy-4-butenoyl-1,3-thiazolidine-4t-butylamide;
  5-isoquinolinoxyacetyl-beta-methylthio-Ala-(2S,3S)-3-amino-2-hydroxy-4-butanoyl-1,3-thiazoildine-4-t-butylamide;
  [1S-[1R-(R-),2S*])N'-3-[[[(1,1-dimethylethyl)amino]carbonyl](2-methylpropyl)amino]-2-hydroxy-1-(phenylmethyl)propyl]-2-[(2-quinolinylcarbonyl)amino]butanediamide;
  amprenavir (VX-478); DMP-323; DMP-450; AG1343 (nelfinavir);
  atazanavir (BMS 232,632);
  tipranavir;
  palinavir;
  darunavir (TMC-114);
  RO033-4649;
  fosamprenavir (GW433908);
  P-1946;
  tert-butyl-[3-hydroxy-4-[2-hydroxy-4-[4-(morpholin-4-ylcarbonylmethoxy)phenyl]-3-tert-butoxycarbonylamino-butyl]amino-1-phenyl-butan-2-yl]aminoformate (BMS 186,318);
  SC-55389a;
  BILA 1906 BS; and
  N-[3-[1-(2-hydroxy-4-oxo-6-phenethyl-6-propyl-5H-pyran-3-yl)propyl]phenyl]-5-(trifluoromethyl)pyridine-2-sulfonamide (tipranavir, U-140690); or combinations thereof.

9. The dosage form of claim 8, wherein said HIV protease inhibitor is (2S,3S,5S)-5-(N—(N—((N-methyl-N-((2-isopropyl-4-thiazolyl)methyl)amino)carbonyl)-L-valinyl) amino-2-(N-((5-thiazolyl)methoxy-carbonyl)-amino) amino-1,6-diphenyl-3-hydroxyhethane (ritonavir).

10. The dosage form of claim 8, wherein said HIV protease inhibitor is (2S,3S,5S)-2-(2,6-dimethyl-phenoxyacetyl)-amino-3-hydroxy-5-[2S-(l-tetrahydro-pyrimid-2-onyl)-3-methylbutanoyl]amino-1,6-diphenylhexane (lopinavir).

11. The dosage form of claim 8, wherein said HIV protease inhibitor is a combination of (2S,3S,5S)-5-(N—(N—((N-methyl-N-((2-isopropyl-4- thiazolyl)methyl)amino)-carbonyl)-L-valinyl)amino-2-(N-((5-thiazoly)methoxy-carbonyl)-amino)-amino-1,6-diphenyl-3-hydroxyhexane (ritonavir) and (2S,3S,5S)-2-(2,6-dimethyl-phenoxyacetyl)-amino-3-hydroxy-5-[2S-(l1-tetrahydro-pyrimid-2-onyl)-3-methylbutanoyl] amino-1,6-diphenylhexane (lopinavir).

12. The solid dosage form of claim 10, wherein said pharmaceutically acceptable homopolymer or copolymer of N-vinylpyrrolidone is a copolymer of-N-vinyl pyrrolidone and vinyl acetate.

13. The solid dosage form of claim 1, containing at least one additive selected from flow regulators, disintegrants, bulking agents and lubricants.

14. The solid dosage form of claim 1, wherein the melt-processed mixture has a Tg of 10° C. or higher.

15. A method of preparing a solid dosage form of claim 5 which comprises:
  (i) preparing a homogeneous melt of said active ingredient(s), said pharmaceutically acceptable hornopolymer(s) or copolymer(s) of N-vinylpyrrolidone and said solubilizing composition, and
  (ii) allowing the melt to solidify to obtain a solid dispersion product.

16. The method of claim 15, additionally comprising grinding said solid dispersion product and compressing said solid dispersion product into a tablet.

17. The method of claim 15, additionally comprising grinding said solid dispersion product and filling said solid dispersion product into a capsule shell.

18. The method of claim 15, wherein the melt is shaped into a film or a foam before being allowed to solidify.

19. The dosage form of claim 1 , wherein the tocopheryl compound (i) is alpha tocopheryl polyethylene glycol succinate and the alkylene glycol fatty acid monoester (ii) is propylene glycol monolaurate.

20. The dosage form of claim 1, wherein the tocopheryl compound (i) is alpha tocopheryl polyethylene glycol succinate, the alkaline glycol fatty acid monoester (ii) is propylene glycol mmol urate and the weight ratio of alpha tocopheryl polyethylene glycol succinate and propylene glycol monolaurate is in the range of from 9:1 to 1:9.

* * * * *